(12) United States Patent
Lunden et al.

(10) Patent No.: US 11,821,883 B2
(45) Date of Patent: Nov. 21, 2023

(54) METHOD FOR DETECTING ANOMALIES IN ENVIRONMENTAL DATA

(71) Applicant: Aclima Inc., San Francisco, CA (US)

(72) Inventors: Melissa M. Lunden, Berkeley, CA (US); Nathan Sankary, Redwood City, CA (US); Shreyan Sen, San Francisco, CA (US); Joshua D. Carr, San Francisco, CA (US); Joshua Richey, Santa Cruz, CA (US); Nicole Goebel, Santa Cruz, CA (US); Meghan Elizabeth Thurlow, San Francisco, CA (US); Davida Herzl, San Francisco, CA (US)

(73) Assignee: Aclima Inc., San Francisco, CA (US)

( * ) Notice: Subject to any disclaimer, the term of this patent is extended or adjusted under 35 U.S.C. 154(b) by 0 days.

(21) Appl. No.: 17/691,608

(22) Filed: Mar. 10, 2022

(65) Prior Publication Data

US 2022/0291184 A1 Sep. 15, 2022

Related U.S. Application Data

(60) Provisional application No. 63/160,233, filed on Mar. 12, 2021.

(51) Int. Cl.
*G01N 33/00* (2006.01)
*G01S 19/01* (2010.01)

(52) U.S. Cl.
CPC .......... *G01N 33/0027* (2013.01); *G01S 19/01* (2013.01)

(58) Field of Classification Search
CPC ........................................................ G01N 1/22
See application file for complete search history.

(56) References Cited

U.S. PATENT DOCUMENTS

| | | | | |
|---|---|---|---|---|
| 2012/0283945 | A1* | 11/2012 | Bird ................... | G01C 21/3492 701/420 |
| 2017/0108350 | A1* | 4/2017 | Nagao .................... | G01D 3/08 |
| 2021/0018210 | A1* | 1/2021 | Nasis ................... | G01N 33/004 |

OTHER PUBLICATIONS deSouza et al., Air quality monitoring using mobile low-cost sensors mounted on trash-trucks: Methods development and lessons learned, Sustainable Cities and Society 60 (Year: 2020).*
J. Brownlee, "A Gentle Introduction to the Bootstrap Method," Machine Learning Mastery, https://machinelearningmastery.com/a-gentle-introduction-to-the-bootstrap-method/, Aug. 8, 2019. Accessed Dec. 17, 2022 (Year: 2019).*

(Continued)

*Primary Examiner* — Ricky Go
(74) *Attorney, Agent, or Firm* — Van Pelt, Yi & James LLP

(57) ABSTRACT

A method for assessing environmental data is described. The method includes receiving sensor data associated with each of a plurality of time intervals from at least one sensor on at least one mobile sensor platform. The sensor data is associated with position data corresponding to each of the plurality of time intervals. The position data corresponds to a plurality of positions having a characteristic distance not exceeding one hundred meters. The sensor data includes a plurality of measurements for each of the plurality of positions. The method includes determining, based on the sensor data and the position data, anomalous data including least one of a geographic anomaly or a temporal anomaly.

17 Claims, 8 Drawing Sheets

(56) References Cited

OTHER PUBLICATIONS

Lunden, M., "Huper-local air quality data to support healthy building design and operation," Sustainable Buildings 2.0, Health buildings and Human Performance, Nov. 7, 2019 (Year: 2019).*
Cummings et al., Mobile Monitoring of Air Pollution Reveals Spatial and Temporal Variation in an Urban Landscape, published May 4, 2021, pp. 1-13.

* cited by examiner

METHOD FOR DETECTING ANOMALIES IN ENVIRONMENTAL DATA

CROSS REFERENCE TO OTHER APPLICATIONS

This application claims priority to U.S. Provisional Patent Application No. 63/160,233 entitled METHOD FOR DETECTING HOT SPOTS IN DATA FROM MOBILE MONITORING PLATFORMS filed Mar. 12, 2021 which is incorporated herein by reference for all purposes.

BACKGROUND OF THE INVENTION

Monitoring of environmental conditions includes measuring the levels of various components of the surroundings. The environmental data collected could facilitate the detection of potentially harmful air pollution, radiation, greenhouse gases or other contaminants in the environment. In order to assess the effects of such pollutants, however, it is desirable to associate environmental data sensing these pollutants at particular times with geographic locations (homes, businesses, towns, etc.) and draw conclusions based on this data. Although such an analysis would allow individuals and communities to evaluate the quality of their surroundings, barriers exist to utilizing the environmental data.

BRIEF DESCRIPTION OF THE DRAWINGS

Various embodiments of the invention are disclosed in the following detailed description and the accompanying drawings.

DETAILED DESCRIPTION

Figure 1:
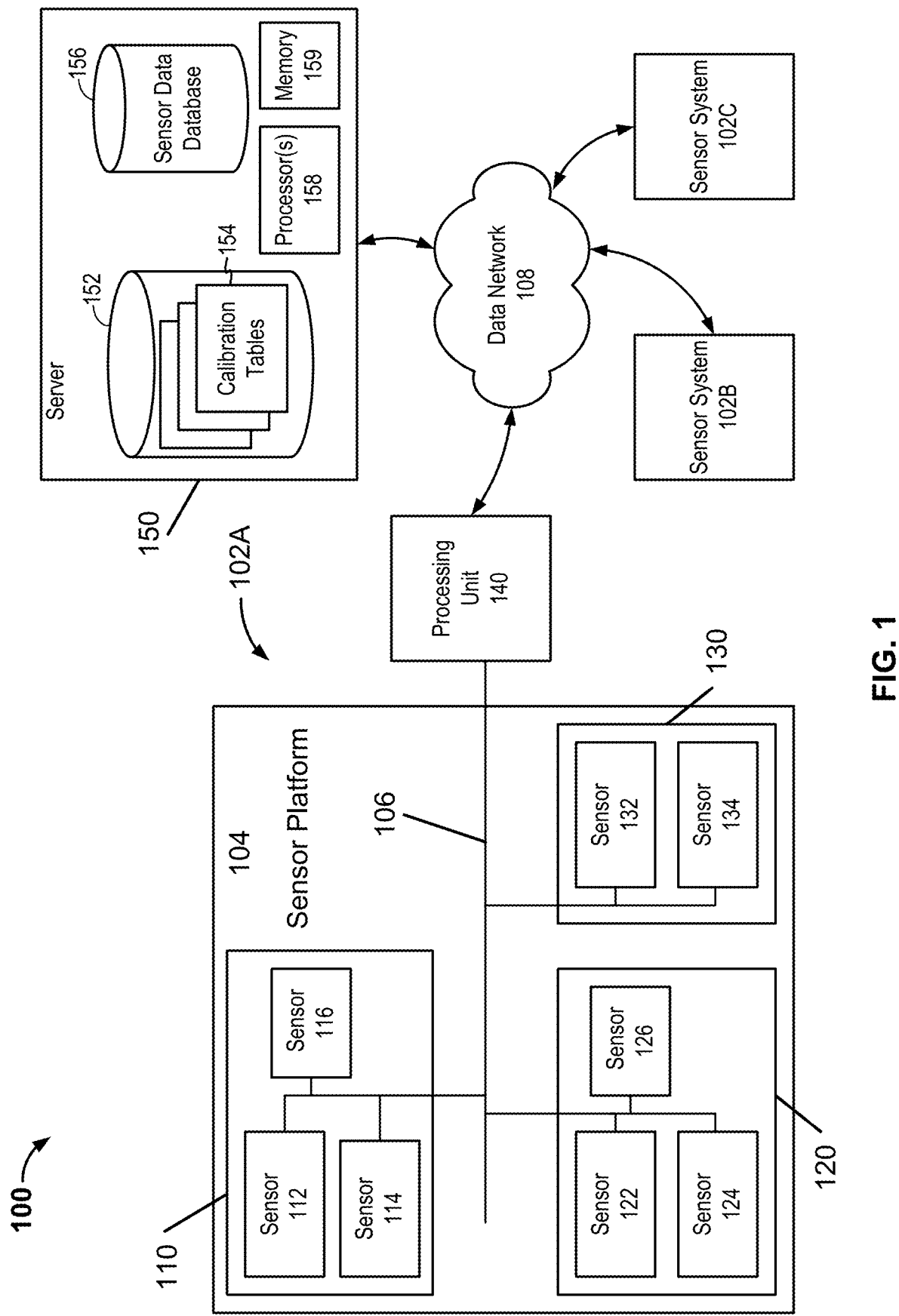
FIG. 1 depicts an embodiment of a system for capturing environmental data using mobile sensor platforms and associating the environmental data with map features.

The invention can be implemented in numerous ways, including as a process; an apparatus; a system; a composition of matter; a computer program product embodied on a computer readable storage medium; and/or a processor, such as a processor configured to execute instructions stored on and/or provided by a memory coupled to the processor. In this specification, these implementations, or any other form that the invention may take, may be referred to as techniques. In general, the order of the steps of disclosed processes may be altered within the scope of the invention. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits, and/or processing cores configured to process data, such as computer program instructions.

A detailed description of one or more embodiments of the invention is provided below along with accompanying figures that illustrate the principles of the invention. The invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

Environmental data includes measurements of pollutants, contaminants and/or other components of the environment. For example, environmental data may be gathered on nitrogen dioxide ($NO_2$), carbon monoxide (CO), nitrogen oxide (NO), ozone ($O_3$), sulphur dioxide ($SO_2$), carbon dioxide ($CO_2$), methane ($CH_4$), volatile organic compounds (VOCs), particulate matter, radiation, noise, temperature, other pathogens and/or other conditions that may affect humans. Environmental data can be used to assess to air quality (e.g. the presence or absence of various pollutants in the air) as well as other features of the surroundings. Thus, environmental data can be used to measure the suitability of the surroundings for humans.

Environmental data may vary based upon a variety of factors such as the pollutant source, intrinsic spatial variations in pollutants, and/or environmental conditions such as the wind, variations in terrain and the presence of man-made structures such as buildings. In addition to variations with geographic location, environmental data can also exhibit temporal variations. For example, meteorological features (e.g. wind, rain, temperature, and barometric pressure) can alter a pollutant's concentration level at a particular location over time. Such variations can occur even if a nearby emission source releases a pollutant at a constant rate. Thus, significant spatial and temporal variations in environmental data may occur. In addition to variations with geographic location, environmental data can also change over time. Due to changing conditions, such as fluctuations in the atmospheric climate, a pollutant's concentration level at a particular location can change over time. Such variations can occur even if a nearby emission source releases a pollutant at a constant rate. Thus, spatial and temporal variations in environmental data may occur.

Individuals and communities may desire to assess the environmental quality in their geographic region. For example, an individual in an urban setting may desire to see how their city compares to other cities or how their neighborhood compares to other neighborhoods in the same city. In some instances, an individual may desire to investigate the environmental quality of their street or home address. Thus, the data for a particular region of interest may be desired to be compared not only to data from other regions, but also to data for the particular region from other times. As part of this comparison, anomalies in the data are desired to be identified and characterized. However, the identification of anomalies with sufficient geographic and temporal sensitivity may be challenging. Further, the confidence in the data and, therefore, the anomalies may also be difficult to determine. Consequently, it may be challenging to associate the anomaly with a real-world condition at a particular time and/or for a particular region, even if high precision sensors provide the environmental data. This may make drawing conclusions about the environmental quality of a region challenging. Consequently, additional techniques for assessing environmental quality are desired.

A method for assessing environmental data is described. The method includes receiving sensor data associated with each of a plurality of time intervals from at least one sensor on at least one mobile sensor platform. The sensor data is associated with position data corresponding to each of the time intervals. The position data corresponds to positions having a characteristic distance not exceeding one hundred meters. The sensor data includes measurements for each of the positions. The method includes determining, based on the sensor data and the position data, anomalous data including a geographic anomaly and/or a temporal anomaly.

In some embodiments, the anomalous data includes the geographic anomaly. In such embodiments, determining the anomalous data further includes determining statistical values for each of the positions for the sensor data. For each of the positions and using a radius greater than the characteristic distance, a Gi* value is determined for each of the statistical values. The geographic anomaly is identified based on the Gi* value of each of the positions. In some embodiments, the anomalous data includes the temporal anomaly. In such embodiments, determining the anomalous data further includes defining a time window. For each time, statistical values are determined for a portion of the sensor data in the time window. The temporal anomaly is identified based on the statistical values. In some such embodiments, the time window is centered at each of the plurality of times. In some such embodiments, the time window has an endpoint on each of the plurality of times.

An uncertainty for a statistical value for the sensor data may also be determined. Determining the uncertainty is performed for the measurements for each position and includes selecting with replacement a number of measurements from the measurements to provide a bootstrap data set; evaluating a corresponding value for the statistical value for the number of measurements in the bootstrap data set; repeating the selecting and evaluating a particular number of times; and identifying the uncertainty based on the corresponding value for each bootstrap data set. In some embodiments, identifying the uncertainty further includes setting upper threshold and lower thresholds. The statistical value is divided by a difference between the upper threshold and the lower threshold. In some embodiments, a cell size is set based on the characteristic distance. A geographic region corresponding to the positions is divided into a plurality of cells having the cell size. For each cell, it is determined whether the plurality of measurements for each of a portion of the plurality of positions for the cell meet particular criteria. In some embodiments, a baseline is determined for the sensor data. The baseline is computed based on the measurements for each of the positions and additional sensor data captured by a sensor data platform different from the at least one mobile sensor platform.

FIG. 1 depicts an embodiment of a system 100 for collecting and processing environmental data. System 100 includes multiple mobile sensor platforms 102A, 102B, 102C and server 150. In some embodiments, system 100 may also include one or more stationary sensor platforms 103, of which one is shown. Stationary sensor platform 103 may be used to collect environmental data at a fixed location. The environmental data collected by stationary sensor platform 103 may supplement the data collected by mobile sensor platforms 102A, 102B and 102C. Thus, stationary sensor platform 103 may have sensors that are the same as or analogous to the sensors for mobile sensor platforms 102A, 102B and 102C. In other embodiments, stationary sensor platform 103 may be omitted. Although a single server 150 is shown, multiple servers may be used. The multiple servers may be in different locations. Although three mobile sensor platforms 102A, 102B and 102C are shown, another number are typically present. Mobile sensor platforms 102A, 102B and 102C and stationary sensor platform(s) 103 may communicate with server 150 via a data network 108. The communication may take place wirelessly.

Mobile sensor platforms 102A, 102B and 102C may be mounted in a vehicle, such as an automobile or a drone. In some embodiments, mobile sensor platforms 102A, 102B and 102C are desired to stay in proximity to the ground to be better able to sense conditions analogous to what a human would experience. Mobile sensor platform 102A includes a bus 106, sensors 110, 120 and 130. Although three sensors are shown, another number may be present on mobile sensor platform 102A. In addition, a different configuration of components may be used with sensors 110, 120 and 130. Each sensor 110, 120 and 130 is used to sense environmental quality and may be of primary interest to a user of system 100. For example, sensors 110, 120 and 130 may be gas sensors, volatile organic compound (VOC) sensors, particulate matter sensors, radiation sensors, noise sensors, light sensors, temperature sensors, noise sensors or other analogous sensors that capture variations in the environment. For example, sensors 110, 120 and 130 may be used to sense one or more of $NO_2$, CO, NO, $O_3$, $SO_2$, $CO_2$, VOCs, CH4, particulate matter, noise, light, temperature, radiation, and other compounds. In some embodiments, sensor 110, 120 and/or 130 may be a multi-modality sensor. A multi-modality gas sensor senses multiple gases or compounds. For example, if sensor 110 is a multi-modality $NO_2/O_3$ sensor, sensor 110 might sense both $NO_2$ and $O_3$ together.

Although not shown in FIG. 1, other sensors co-located with sensors 110, 120 and 130 may be used to sense characteristics of the surrounding environment including, in some instances, other gases and/or matter. Such additional sensors are exposed to the same environment as sensors 110, 120 and 130. In some embodiments, such additional sensors are in close proximity to sensors 110, 120 and 130, for example within ten millimeters or less. In some embodiments, the additional sensors may be further from sensors 110, 120 and 130 if the additional sensors sample the same packet of air inside of a closed system, such as a system of closed tubes. In some embodiments, temperature and/or pressure are sensed by these additional sensors. For example, an additional sensor co-located with sensor 110 may be a temperature, pressure, and relative humidity (T/P/RH) sensor. These additional co-located sensors may be used to calibrate sensors 110, 120 and/or 130. Although not shown, sensor platform 102A may also include a manifold for drawing in air and transporting air to sensors 110, 120 and 130 for testing.

Sensors 110, 120 and 130 provide sensor data over bus 106, or via another mechanism. In some embodiments, data from sensors 110, 120 and 130 incorporates time. This time may be provided by a master clock (not shown) and may take the form of a timestamp. Master clock may reside on sensor platform 102A, may be part of processing unit 140, or may be provided from server 150. As a result, sensors 110, 120 and 130 may provide timestamped sensor data to server 150. In other embodiments, the time associated with the sensor data may be provided in another manner. Because sensors 110, 120 and 130 generally capture data at a particular frequency, sensor data is discussed as being associated with a particular time interval (e.g. the period associated with the frequency), though the sensor data may be timestamped with a particular value. For example, sensors 110, 120 and/or 130 may capture sensor data every second, every two seconds, every ten seconds, or every thirty seconds. The time interval may be one second, two seconds, ten seconds, or thirty seconds. The time interval may be the same for all sensors 110, 120 and 130 or may differ for different sensors 110, 120 and 130. In some embodiments, the time interval for a sensor data point is centered on the timestamp. For example, if the time interval is one second and a timestamp is t1, then the time interval may be from t1−0.5 seconds to t1+0.5 seconds. However, other mechanisms for defining the time interval may be used.

Sensor platform 102A also includes a position unit 145 that provides position data. In some embodiments, position unit 145 is a global positioning satellite (GPS) unit. Consequently, system 100 is described in the context of a GPS unit 145. The position data may be time-stamped in a manner analogous to sensor data. Because position data is to be associated with sensor data, the position data may also be considered associated with time intervals, as described above. However, in some embodiments, position data (e.g. GPS data) may be captured more or less frequently than sensor data. For example, GPS unit 145 may capture position data every second, while sensor 130 may capture data every thirty seconds. Thus, multiple data points for the position data may be associated with a single thirty second time interval. The position data may be processed as described below.

Optional processing unit 140 may perform some processing and functions for data from sensor platform 104, may simply pass data from sensor platform 104 to server 150 or may be omitted.

Mobile sensors platforms 102B and 102C are analogous to mobile sensor platform 102A. In some embodiments, mobile sensor platforms 102B and 102C have the same components as mobile sensor platform 102A. However, in other embodiments, the components may differ. However, mobile sensor platforms 102A, 102B and 102C function in an analogous manner.

Server 150 includes sensor data database 152, processor(s) 154, memory 156 and position data database 158. Processor(s) 154 may include multiple cores. Processor(s) 154 may include one or more central processing units (CPUs), one or more graphical processing units (GPUs) and/or one or more other processing units. Memory 156 can include a first primary storage, typically a random-access memory (RAM), and a second primary storage area, typically a non-volatile storage such as solid-state drive (SSD) or hard disk drive (HDD). Memory 156 stores programming instructions and data for processes operating on processor(s) 154. Primary storage typically includes basic operating instructions, program code, data and objects used by processor(s) 154 to perform their functions. Primary storage devices (e.g., memory 156) may include any suitable computer-readable storage media, described below, depending on whether, for example, data access needs to be bi-directional or uni-directional Sensor data database 152 includes data received from mobile sensor platforms 102A, 102B and/or 102C. After capture by mobile sensor platform 102A, 102B and/or 102C, sensor data stored in sensor data database 152 may be operated on by various analytics, as described below. Position data database 158 stores position data received from mobile sensor platforms 102A, 102B and/or 102C. In some embodiments, sensor data database 152 stores position data as well as sensor data. In such embodiments, position data database 158 may be omitted. Server 150 may include other databases and/or store and utilize other data. For example, server 150 may include calibration data (not shown) used in calibrating sensors 110, 120 and 130.

System 100 may be used to capture, analyze, and provide information regarding hyper-local environmental data. Mobile sensor platforms 102A, 102B and 102C may be used to traverse routes and provide sensor and position data to server 150. Server 150 may process the sensor data and position data. Server 150 may also assign the sensor data to map features corresponding to the locations of mobile sensor platforms 102A, 102B and 102C within the same time interval as the sensor data was captured. As discussed above, these map features may be hyper-local (e.g. one hundred meter or less road segments or thirty meter or less road segments). Thus, mobile sensor platforms 102A, 102B and 102C may provide sensor data that can capture variations on this hyper-local distance scale. Server 150 may provide the environmental data, a score, confidence score and/or other assessment of the environmental data to a user. Thus, using system 100 hyper-local environmental data may be obtained using a relatively sparse network of mobile sensor platforms 102A, 102B and 102C, associated with hyper-local map features and processed for improved understanding of users.

Figure 2:
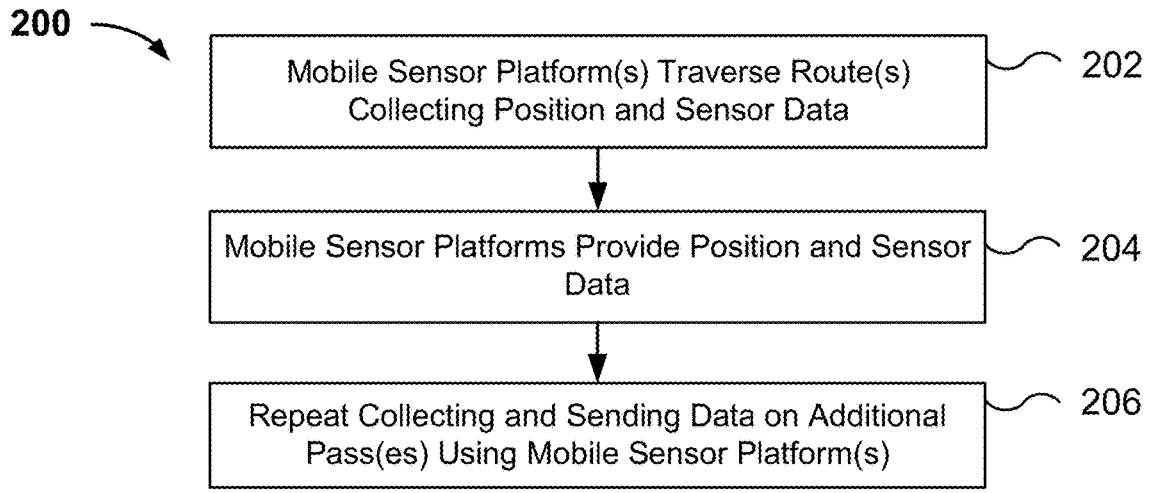
FIG. 2 depicts an embodiment of a method for capturing environmental data using mobile sensor platforms.

FIG. 2 depicts an exemplary embodiment of method 200 for capturing environmental data using mobile sensor platforms, such as mobile sensor platforms 102A, 102B and/or 102C. Method 200 is described in the context of system 100, but may be performed using other systems. For clarity, only some portions of method 200 are shown. Although shown in a sequence, in some embodiments, processes may occur in parallel and/or in a different order.

Mobile sensor platforms traverse routes in a geographic region, at 202. While traversing the routes, the mobile sensor platforms collect not only sensor data, but also position data. For example, a mobile sensor platform may sense one or more of $NO_2$, CO, NO, $O_3$, $SO_2$, $CO_2$, $CH_4$, VOCs, particulate matter, other compounds, radiation, noise, light, and other environmental data at various times during traversal of the route. Other environmental characteristics, including but not limited to temperature, pressure, and/or humidity may also be sensed at 202. In addition, the time corresponding to the environmental data is also captured. The time may be in the form of a timestamp for the sensor data (sensor timestamp), which may correspond to a particular time interval. Different sensors on the mobile sensor platform may capture the environmental data at different times and/or at different frequencies. Also at 202 the mobile sensor platforms capture position data, for example via a GPS unit. The position data may include location (as indicated by a GPS unit), velocity and/or other information related to the geographic location of the mobile sensor platform. In some embodiments, position data from other sources, such as acceleration, may be captured from by the vehicle or another source. The position data may include a timestamp (position timestamp) or other indicator of the time at which the position data is captured.

The mobile sensor platforms provide the position and sensor data to a server, at 204. In some embodiments, mobile sensor platforms provide this data substantially in real time, as the mobile sensor platforms traverse their routes at 202. Thus, the position and sensor data may be transmitted wirelessly to the server. In some embodiments, some or all of the position and/or sensor data is stored at the mobile sensor platform and provided to the server at a later time. For example, the data may be transferred to the server when the mobile sensor platform returns to its base. In some embodiments, the mobile sensor platform may process the sensor data and/or position data prior to sending the sensor and/or position data to the server. In other embodiments, the mobile sensor platform provides little or no processing. The sensor data and position data may be sent at the same time or may be sent separately.

At 206, the route traversal and data collecting of 202 and data sending of 204 are repeated. Thus, the mobile sensor platforms may traverse the same or different routes at 206. In either case, multiple passes of the same geographic locations, and thus multiple passes of the same corresponding map features, are made at 206. In some embodiments, the repetition at 206 may be periodic (e.g. approximately every week, month, or other time period). In some embodiments, the repetition at 206 may be performed based on other timing. In some cases, the same mobile sensor platform is sent on the same route and/or collects data for the same map features. In some embodiments, different mobile sensor platforms collect data may be used for the same routes and/or map features. Also at 206, steps 202 and 204 may be performed multiple times. Thus, at 206, data for a particular region may be aggregated over time.

Figure 3A:
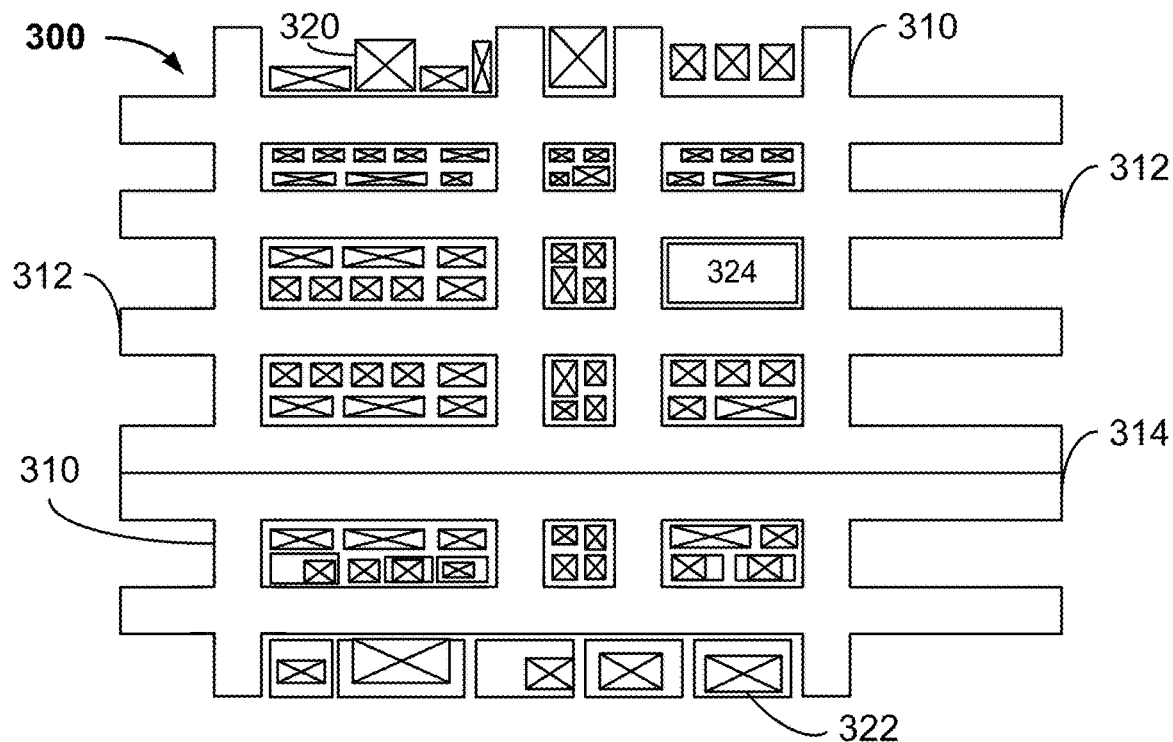
FIGS. 3A-3C illustrate a particular region and the embodiment of routes that may be traversed using a method for capturing environmental data using mobile sensor platforms.
Figure 3B:
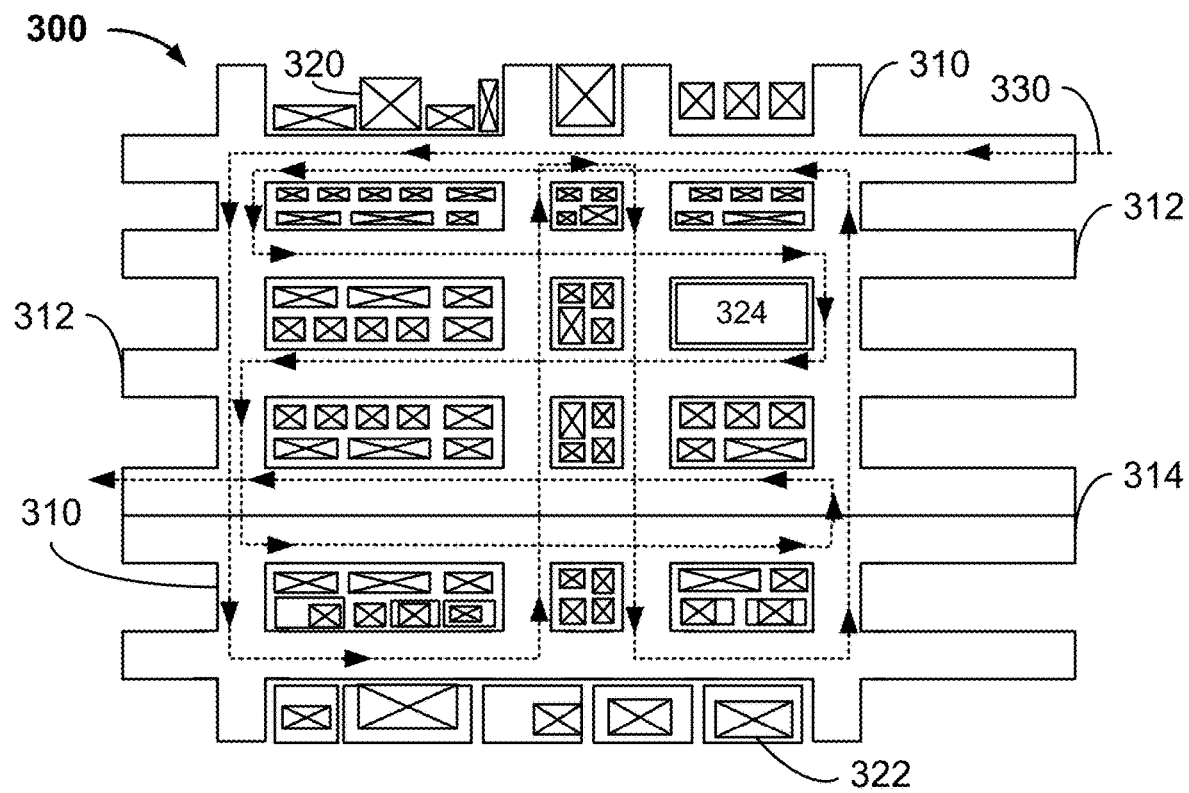
Figure 3C:
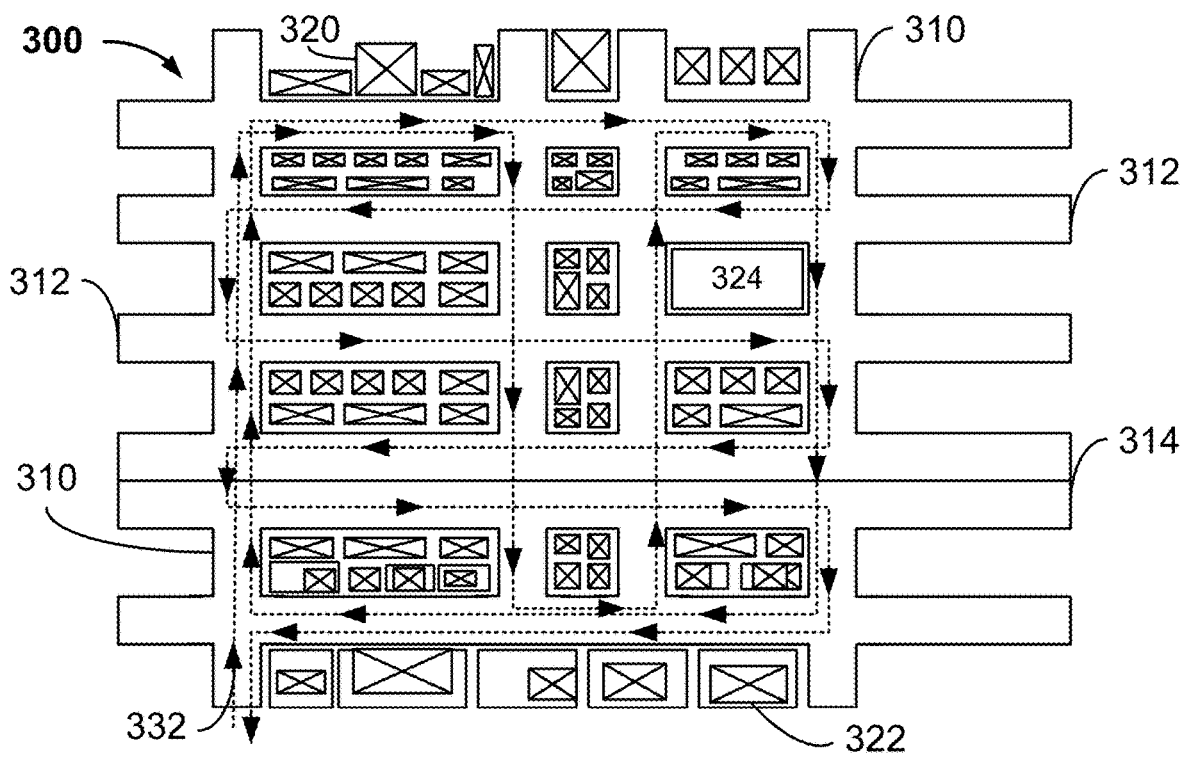

For example, FIGS. 3A-3C illustrate a particular geographic region and the routes that may be traversed using method 200. A map 300 corresponding to the geographic region is shown in FIG. 3A. Map 300 may be an open-source map or generated by another mapping tool. Map 300 includes streets 310 (oriented vertically on the page) and 312 (oriented horizontally on the page); larger street/highway 314, structures 320 and 322 and open area 324. For simplicity, only one of each structure 320 and 322 is labeled. Open area 324 may correspond to a park, vacant lot, or analogous item. As can be seen in FIG. 3A, the density and size of structures 320 and 322 vary across map 300. Similarly, the density and size of streets 312, 314 and 320 also varies. In addition, structures 322 are more clearly separated by open regions, which may correspond to a yard or analogous area.

FIG. 3B illustrates map 300 as well as route 330 that may be traversed by a mobile sensor platform, such as mobile sensor platform 102A. At 202, mobile sensor platform 102A may traverse route 330. As can be seen in FIG. 3B, the route 330 includes a portion of each street 312 and 314 in map 300. Some portions of some streets are traversed multiple times for the same route 330. In some embodiments, this is still considered a single pass of these streets. As mobile sensor platform 102A traverses route 330 at 202, sensor data is captured by sensors 110, 120 and 130. Also at 202, position data is captured by GPS unit 145 throughout route 330. In some embodiments, the vehicle carrying mobile sensor platform 102A travels sufficiently slowly while traversing route 330 that sensor data and position data can be accurately captured for particular position(s). In some embodiments, mobile sensor platform 102A travels at a velocity that allows for multiple sensor data points for each map feature. Mobile sensor platform 102A also sends position and sensor data to server 150 at 204. This may be done while mobile sensor platform 102A traverses route 330 or at a later time. Other mobile sensor platforms 102B and/or 102C may also traverse the same or different routes and send data to server 150 at 202 and 204. Thus, multiple mobile sensor platforms may be used in method 200.

At 206, mobile sensor platform 102A and/or other mobile sensor platform(s) 102B and 102C repeat the route traversal, data collection and sending of the position and sensor data. In some cases, mobile sensor platform(s) 102A, 102B and/or 102C follow route 330 again. In some cases, mobile sensor platform(s) 102A, 102B and/or 102C traverses a different route. For example, FIG. 3C depicts map 300 with another route 332. As part of 206, mobile sensor platform(s) 102A, 102B and/or 102C may traverse route 332, collecting position and sensor data at 206 (repeating 202). In some embodiments, the vehicle carrying mobile sensor platform(s) 102A, 102B and/or 102C travels sufficiently slowly while traversing route 332 that sensor data and position data can be accurately captured for particular position(s). In some embodiments, mobile sensor platform(s) 102A, 102B and/or 102C travels at a velocity that allows for multiple sensor data points for each map feature (described below). Mobile sensor platform(s) 102A, 102B and/or 102C send sensor and position data to server 150 at 206 (repeating 204) during or after traversing route 330 and/or route 332.

Thus, using method 200, sensor and position data may be captured for regions of a map. The sensor data and position data may be provided to server 150 or other component for processing, aggregation, and analysis. Sensor data and position data are sensed sufficiently frequently using method 200 that variations environmental quality on the hyper-local scales may be reflected in the sensor data. Method 200 may be performed using a relatively small number of mobile sensor platforms. Consequently, efficiency of data gathering may be improved while maintaining sufficient sensitivity in both sensor and position data.

For example, FIGS. 3A-3C illustrate a particular geographic region and the routes that may be traversed using method 200. A map 300 corresponding to the geographic region is shown in FIG. 3A. Map 300 may be an open-source map or generated by another mapping tool. Map 300 includes streets 310 (oriented vertically on the page) and 312 (oriented horizontally on the page); larger street/highway 314, structures 320 and 322 and open area 324. For simplicity, only one of each structure 320 and 322 is labeled. Open area 324 may correspond to a park, vacant lot, or analogous item. As can be seen in FIG. 3A, the density and size of structures 320 and 322 vary across map 300. Similarly, the density and size of streets 312, 314 and 320 also varies. In addition, structures 322 are more clearly separated by open regions, which may correspond to a yard or analogous area.

FIG. 3B illustrates map 300 as well as route 330 that may be traversed by a mobile sensor platform, such as mobile sensor platform 102A. At 202, mobile sensor platform 102A may traverse route 330. As can be seen in FIG. 3B, the route 330 includes a portion of each street 312 and 314 in map 300. Some portions of some streets are traversed multiple times for the same route 330. In some embodiments, this is still considered a single pass of these streets. As mobile sensor platform 102A traverses route 330 at 202, sensor data is captured by sensors 110, 120 and 130. Also at 202, position data is captured by GPS unit 145 throughout route 330. In some embodiments, the vehicle carrying mobile sensor platform 102A travels sufficiently slowly while traversing route 330 that sensor data and position data can be accurately captured for particular position(s). In some embodiments, mobile sensor platform 102A travels at a velocity that allows for multiple sensor data points for each map feature. Mobile sensor platform 102A also sends position and sensor data to server 150 at 204. This may be done while mobile sensor platform 102A traverses route 330 or at a later time. Other mobile sensor platforms 102B and/or 102C may also traverse the same or different routes and send data to server 150 at 202 and 204. Thus, multiple mobile sensor platforms may be used in method 200.

At 206, mobile sensor platform 102A and/or other mobile sensor platform(s) 102B and 102C repeat the route traversal, data collection and sending of the position and sensor data. In some cases, mobile sensor platform(s) 102A, 102B and/or 102C follow route 330 again. In some cases, mobile sensor platform(s) 102A, 102B and/or 102C traverses a different route. For example, FIG. 3C depicts map 300 with another route 332. As part of 206, mobile sensor platform(s) 102A, 102B and/or 102C may traverse route 332, collecting position and sensor data at 206 (repeating 202). In some embodiments, the vehicle carrying mobile sensor platform(s) 102A, 102B and/or 102C travels sufficiently slowly while traversing route 332 that sensor data and position data can be accurately captured for particular position(s). In some embodiments, mobile sensor platform(s) 102A, 102B and/or 102C travels at a velocity that allows for multiple sensor data points for each map feature (described below). Mobile sensor platform(s) 102A, 102B and/or 102C send sensor and position data to server 150 at 206 (repeating 204) during or after traversing route 330 and/or route 332.

Thus, using method 200, sensor and position data may be captured for regions of a map. The sensor data and position data may be provided to server 150 or other component for processing, aggregation, and analysis. Sensor data and position data are sensed sufficiently frequently using method 200 that variations environmental quality on the hyper-local scales may be reflected in the sensor data. Method 200 may be performed using a relatively small number of mobile sensor platforms. Consequently, efficiency of data gathering may be improved while maintaining sufficient sensitivity in both sensor and position data.

Figure 4:
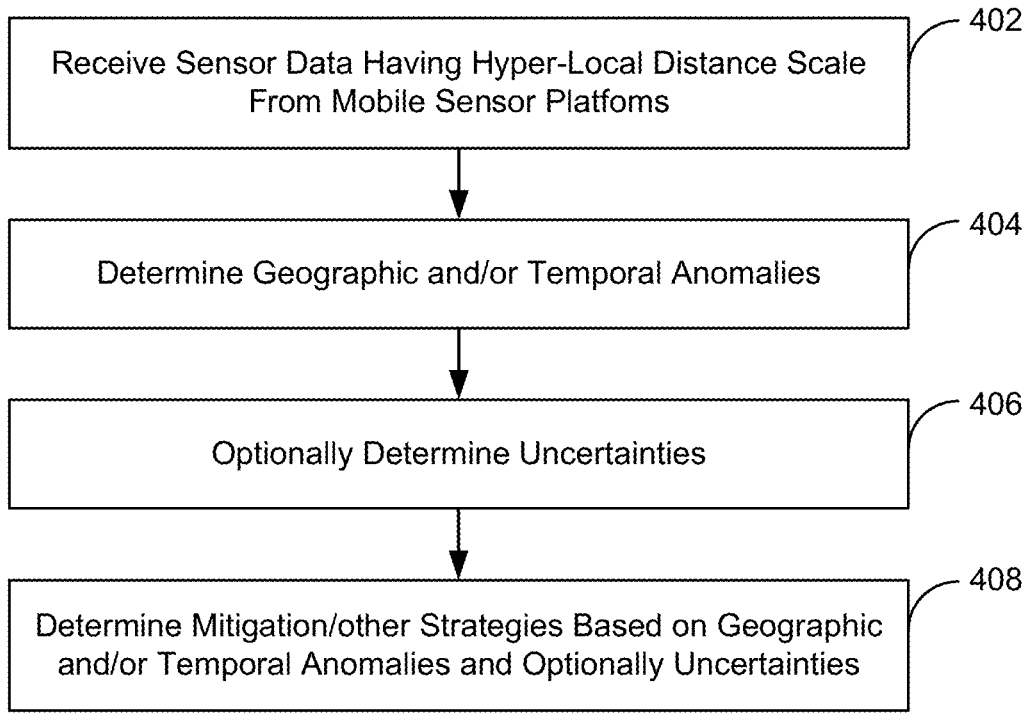
FIG. 4 is a flow chart depicting an embodiment of a method for determining anomalies in environmental data.

FIG. 4 is a flow chart depicting an embodiment of method 400 for determining anomalies in environmental data. Method 400 uses environmental data captured using mobile sensor platforms, such as mobile sensor platforms 102A, 102B and/or 102C. Method 400 is described in the context of system 100 but may be performed using other systems. For clarity, only some portions of method 400 are shown. Although shown in a sequence, in some embodiments, processes may occur in parallel and/or in a different order. The sensor data described herein may include environmental and/or air quality data including but not limited to particulate matter and gases described herein. Further, method 400 utilizes hyper-local data such as that captured using method 200. For example, the sensor data may be associated with positions at hyper-local distance scales (e.g. road segments and/or cells having a characteristic distance of not more than 100 meters, not more than fifty meters, or not more than thirty meters). There may also be multiple data points taken close together in time (e.g. every second, every two seconds, every ten seconds, or every thirty seconds). Consequently, in regions where the environmental data is collected by sensors on the mobile sensor platform, the data may be dense geographically (i.e. hyper-local) and temporally. However, the entire data set may still omit areas in the region of interest. For example, for data being capture for a city, a park or other region in which mobile sensor platforms are not driven may be omitted or may have less data (e.g. fewer points that may be spaced further apart in time and/or distance) collected.

Sensor data is received, at 402. The sensor data was captured by one or more sensors on the mobile sensor platform(s) and may be received at a server. The sensor data includes environmental data. For example, the sensor data may be for particulate matter having a characteristic length of not more than 2.5 micrometers (i.e. PM2.5), nitrogen dioxide ($NO_2$), carbon monoxide (CO), nitrogen oxide (NO), ozone ($O_3$), sulphur dioxide ($SO_2$), carbon dioxide ($CO_2$), methane ($CH_4$), volatile organic compound (VOC), radiation, noise, temperature, humidity, pressure, other pathogens and/or other conditions. Each data point in the sensor data may have a timestamp (i.e. a sensor timestamp). Thus, the sensor data is associated with time intervals. The amount of time between sensor timestamps may correspond to the time interval. In some embodiments, different sensors may have different time intervals. The time intervals may be based upon the response time, or time constant, of the sensor. The response time of a sensor may be affected by how rapidly a flow moves the sampling lines for a sensor as well as the time taken by the sensor itself to complete an observation. For example, a sensor that takes a relatively long time (e.g. up to thirty seconds) to collect data (e.g. a long time constant) may have a thirty second time interval, while a sensor that can more rapidly sense data (e.g. every two seconds, for a shorter response time) may have a two second time interval.

Position data is also received from mobile sensor platform(s), at 402. The position data may be gathered by a GPS unit and received by a server. Each data point of the position data may have a timestamp (position timestamp). The sensor timestamps in the sensor data may differ from the position timestamps in the position data because sensor data and position data may be captured data different times. Thus, data collected and sent using method 200 may be received at 402.

Anomalies in the sensor data are determined, at 404. In some embodiments, 404 includes processing the sensor data (e.g. environmental and position data). Processing the data may include associating the environmental data with geographic features having hyper-local distance scales (e.g. not more than one hundred meters, not more than fifty meters, or not more than thirty meters). To do so, the trajectories and corrected locations for the mobile sensor platform that provided the data may be generated using the position data. Locations provided directly from a GPS unit may be unreliable in urban settings. If the GPS data is not corrected, an erroneous position (e.g. a different street or block) may be associated with the sensor data. Thus, the GPS data is used to generate a trajectory. In some embodiments, the position timestamps and GPS data points (the combination of which may be considered analogous to a velocity/speed and direction) are used to establish the trajectory. The trajectory in combination with other GPS data is used to provide a corrected location. Thus, a more accurate determination of the location of the mobile sensor platform(s) can be made. In cases in which the GPS or other data used is determined to be sufficiently accurate, generating trajectories and correcting the location may be omitted. Based on the corrected location (or location) and trajectory, the location of the mobile sensor platform is assigned to a position for each time interval. For example, the corrected location of mobile sensor platform may be assigned to a particular segment of a road (road segment), to a particular area (cell), to a particular address, particular latitude and longitude ranges, or other section of a map for the corresponding position timestamp. Sensor data captured while the within this position (e.g. segment) is associated with the position (e.g. segment). This means that multiple data points for a particular sensor may be assigned to the same segment. For example, a sensor may capture data at one second intervals. It may take five seconds for the mobile sensor platform (i.e. the vehicle in which the mobile sensor platform is mounted) to traverse a segment that is one hundred meters in length. In this instance, five data points for the sensor may be assigned to the same segment. Thus, the sensor data is assigned to a position that has hyper-local distance scales. Consequently, at least some of the sensor data received may be considered to be at the hyper-local distance scales and time intervals described herein. In other embodiments, the sensor data may be assigned to positions having other (e.g. longer) distance scales.

Processing the sensor data to identify the anomalies at 404 may also include calibrating the sensor data and determining statistical values corresponding to the sensor data. For example, means, medians, percentile(s), standards of deviation and/or other statistical values are determined. The statistical values may be determined based on position (e.g. the median nitrogen dioxide value for a particular road segment), time (e.g. the median PM2.5 value for a ten-minute time window around a particular time stamp), or some combination thereof. In some embodiments, the statistical values are evaluated with respect to a baseline (or background), instead of or in addition to raw measurements. The baseline may be determined based on the sensor data collected in a larger region over a longer time than a single sampling run and/or based on data from other sources. For example, data collected for a city or county over an entire day, week, month, year, or quarter may be used in determining the baseline. Other sources that may be used in lieu of or in addition to the sensor data may include regulatory data, models (e.g. traffic models in conjunction with engine emission profiles), satellite data, meteorological data, and/or data from stationary sensor platforms. In such embodiments, the geographic and/or temporal anomalies may be determined based on a difference between the measured or statistical values and the baseline. Thus, the anomalies determined at 404 may be anomalies in aggregated data (e.g. anomalies in medians or means) and/or anomalies in raw data (as calibrated or otherwise processed). Further, the anomalies may be with respect to geography (e.g. a collection of road segments or cells having differing values for the entire data set captured over some longer time), with respect to time (e.g. differing values for particular position(s) for a transient time in comparison to the time period over which the entire data set was captured), or with respect to geography and time.

In some embodiments, uncertainties in the statistical values and/or identification of anomalies is determined, at 406. In some embodiments, 406 may be omitted. Determination of uncertainties may include the processing of data to determine standards of deviation and analogous statistical measures. In some embodiments, precision in the data from individual sensors is expressly incorporated into the determination of the uncertainties at 406. Other and/or additional techniques may be used to indicate the uncertainties in the statistical values and the confidence with which the anomalies are identified.

In some embodiments, mitigation and/or other strategies are determined based on the geographic and/or temporal anomalies that are detected, at 408. The uncertainties may also be incorporated into the identification of such strategies. For example, for positive anomaly in the methane detected (i.e. more methane present) for a set of road segments that is very transient in time and/or has significant associated uncertainties, no mitigation may be performed. In contrast, for a positive anomaly in methane detected for the set of road segments that persists for a longer period of time and has low associated uncertainties, a mitigation strategy may be developed. For example, the region may be searched for natural gas leaks and any leaks found fixed.

Using method 400, anomalies in environmental data may be better and more readily identified based on hyper-local environmental data. Moreover, the anomalies themselves may be localized in nature (e.g. in a small number of road segments/a hyper-local geographic area and/or limited in time). Consequently, the presence or absence of particular constituents in the environment may be more readily determined and mitigation strategies may be better matched to the particular anomaly.

Figure 5:
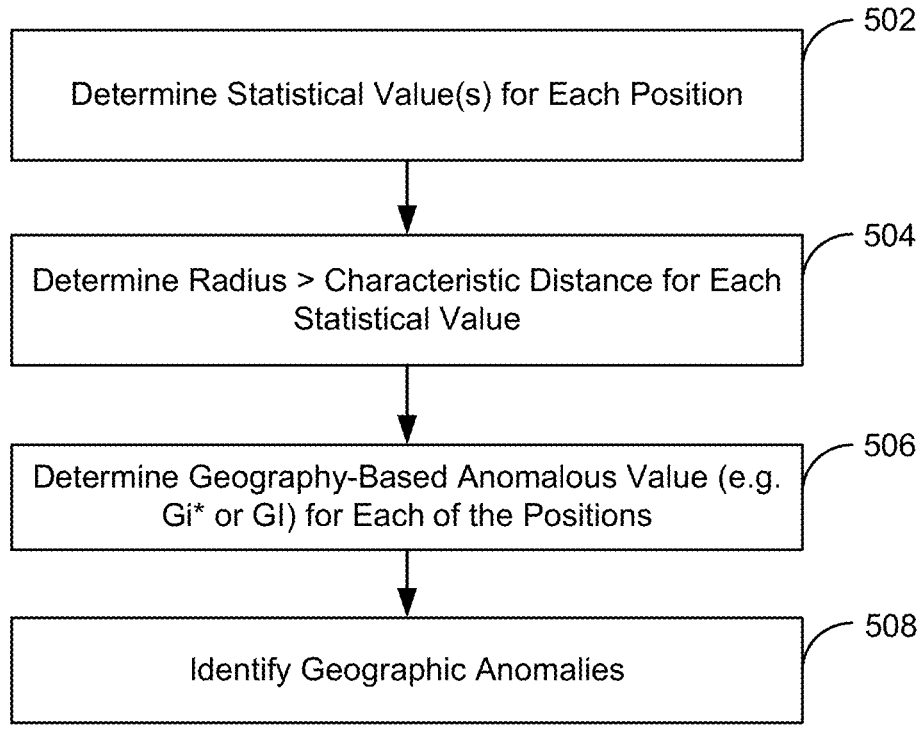
FIG. 5 is a flow chart depicting an embodiment of a method for determining geographic anomalies in environmental data.

FIG. 5 is a flow chart depicting an embodiment of method 500 for determining geographic anomalies in environmental data. Method 500 uses environmental data captured using mobile sensor platforms, such as mobile sensor platforms 102A, 102B and/or 102C. Method 500 is described in the context of system 100 but may be performed using other systems. For clarity, only some portions of method 500 are shown. Although shown in a sequence, in some embodiments, processes may occur in parallel and/or in a different order. The sensor data described herein may include environmental and/or air quality data including but not limited to particulate matter and gases described herein. Further, method 500 utilizes hyper-local data such as that captured using method 200 and processed as described in method 400. Method 500 may be considered to include some or all of 404 of method 400.

Statistical values for the sensor data are determined for each of the positions, at 502. For example, 502 may include determining the median, mean, and distribution in PM2.5 and/or CO measurements for road segments in a region. Thus, data of interest is aggregated and processed at 502. At 504, a radius is determined. The radius is greater than the characteristic distance for the hyper-local sensor data. Further, the radius is significantly less than the size of the region for which sensor data is collected. The radius selected may also depend upon the type of data for which method 500 is performed. For example, the radius selected for PM2.5 data may be different from the radius selected for radiation data (e.g. the radius for PM2.5 data might be greater than the radius for radiation data), $NO_2$ data, temperature data (e.g. the radius for PM2.5 data might be less than the radius for temperature data), and/or humidity data (e.g. the radius for PM2.5 data might be less than the radius for humidity data). In some embodiments, the radius is equal to or greater than one hundred and fifty meters (e.g. equal to or greater than 1.5 multiplied by the characteristic distance). In some embodiments, the radius is two hundred meters or more (e.g. approximately equal to or greater than two hundred meters equal to or greater than two multiplied by the characteristic distance). In some embodiments, the radius is equal to or greater than five hundred meters (e.g. approximately or greater than five multiplied by the characteristic distance).

The radius may not scale with the characteristic distance. In addition, the statistical values calculated at 502 are associated with a point in the characteristic distance. For example, the statistical values may be associated with the centroid or an endpoint of a road segment. The radius selected at 504 defines an area around the point.

A geography-based anomalous value is determined for the statistical value(s) of the positions (e.g. the centroids of the road segments), at 506. The geography-based anomalous value indicates whether there is a geographic anomaly in the statistical value(s) at the position. A geographic anomaly at a position may indicate that some or all of the statistical value(s) for that position or a specified region around that position (e.g. a number of segments adjoining or near the current segment) varies from that of a broader region (e.g. a route, a city, or a county for which data is collected). In some embodiments, geography-based anomalous values are determined for the mean, median, maximum, seventy-fifth quantile, eighty-fifth quantile, and/or ninety-fifth quantile. Other values and/or quantiles may be used in some embodiments. For example, use of the seventy-fifth and/or eighty-fifth quantile indicates where concentrations of a particular environmental constituent are high but are less dependent upon maximum values (which may be outliers). In contrast, use of the fifteenth or twenty-fifth quantile indicates where concentrations of a particular environmental constituent are low but are less dependent upon minimum values (which may be outliers). These geography-based anomalous values may be used for a single environmental constituent (e.g. PM2.5 only) or multiple environmental constituents (e.g. PM2.5, $NO_2$, $CO_2$, CO, etc.) at the positions. In some embodiments, 506 is performed for all positions. In some embodiments, the positions for which 506 is performed fulfill other criteria. In some embodiments, the geography-based anomalous value is determined only for positions having a sufficient amount of data. For example, 506 might be carried out only for road segments having at least twenty passes (i.e. twenty separate data collections). For clarity, the discussion assumes all positions meet any criteria.

In some embodiments, 506 includes determining the Gi* value for statistical value(s) of each position. The Gi* value may be given by:

$$G(i)^* = \frac{\sum_{j=1}^{n} w_{i,j} x_j - \bar{x} \sum_{j=1}^{n} w_{i,j}}{S \sqrt{\frac{n \sum_{j=1}^{n} w_{i,j}^2 - \left(\sum_{j=1}^{n} w_{i,j}\right)^2}{n-1}}} \quad \text{where:} \quad [1]$$

$$\bar{x} = \frac{1}{n} \sum_{j=1}^{n} x_j \quad [2]$$

$$S = \sqrt{\frac{1}{n}\left(\sum_{j=1}^{n} x_j^2\right) - \bar{x}^2} \quad [3]$$

where $x_j$ is the statistical value at point j, all points (positions) are indexed from 1 to n, $w_{i,j}$ is the weight value associated with two positions, S is the standard deviation, and $\bar{x}$ is the mean.

The Gi* value for a particular position indicates whether statistical values for the area centered at the position and within the radius are unexpected in comparison to statistical values for the entire region analyzed. Thus, the Gi* is geographically based only. Temporal variations (e.g. how values at a particular position change over time) are not considered. For example, for the statistical value being the medians for PM2.5 data, the Gi* value for a road segment indicates whether the medians in PM2.5 data for the region centered at the centroid of the road segment and including all road segments having centroids within the radius are anomalous in comparison to the medians in PM2.5 data for the entire region. In some embodiments, 506 includes determining the Gi value. The Gi value is analogous to the Gi* value but does not include data for the center of the circle. In some embodiments, a threshold p-value is also used. The p-value indicates whether the anomaly is likely to be statistically significant. Thus, in some embodiments, the determination at 506 includes utilizing a threshold p-value of 0.05 (e.g. p-values less than 0.05 or p-value not greater than 0.05). In some embodiments, the threshold p-value is 0.01. Also in some embodiments, only positive Z-scores (the observed value being greater than the mean) are used. Although the Gi* value is determined using a geo-spatial technique, the GI* technique may be constructed to iterate over temporal features. For example, Gi* values from different time periods may be compared to identify and/or determine characteristics of anomalies with respect to both space and time. Other techniques may be used to incorporate the Gi* value into temporal analysis.

The geographic anomaly is identified based on the geography-based anomalous value (e.g. the Gi* value) of each of the positions, at 508. As a result, the anomalies may be determined.

Using method 500, geographic anomalies in the environmental data may be determined. Further, method 500 may result in a more accurate determination of anomalies. For example, fewer false positives than other techniques may be detected. Specific areas within the radius can be compared to the region as a whole. Moreover, method 500 may be utilized where data for portions of the region of interest is sparse. Because geographic anomalies may be better identified using method 500, mitigation and other strategies may also be more readily identified. Thus, drawing conclusions from the environmental data is also facilitated.

Figure 6:
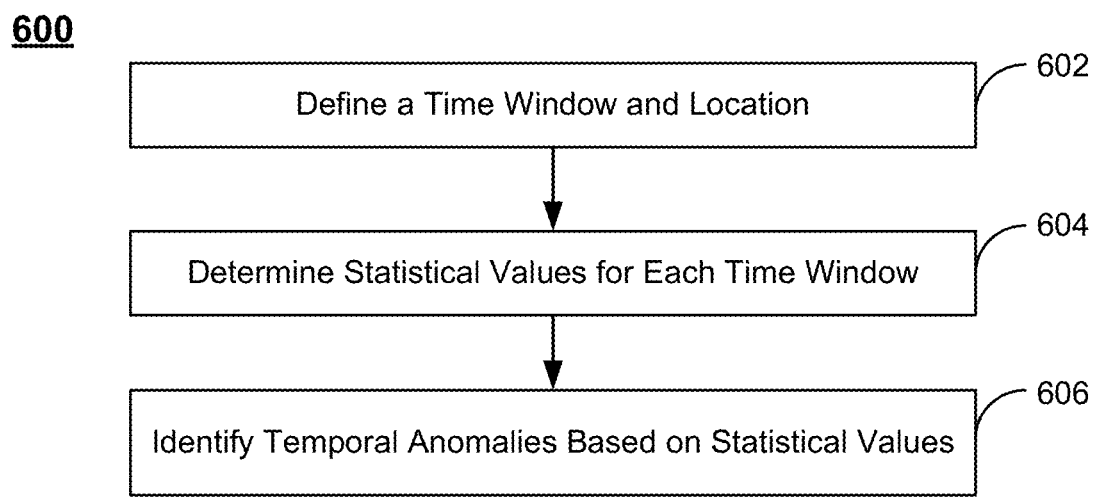
FIG. 6 is a flow chart depicting an embodiment of a method for determining temporal anomalies in environmental data.

FIG. 6 is a flow chart depicting an embodiment of method 600 for determining temporal anomalies in environmental data. Method 600 uses environmental data captured using mobile sensor platforms, such as mobile sensor platforms 102A, 102B and/or 102C. Method 600 is described in the context of system 100 but may be performed using other systems. For clarity, only some portions of method 600 are shown. Although shown in a sequence, in some embodiments, processes may occur in parallel and/or in a different order. The sensor data described herein may include environmental and/or air quality data including but not limited to particulate matter and gases described herein. Further, method 600 utilizes hyper-local data such as that captured using method 200 and processed as described in method 400. Method 600 may be considered to include some or all of 404 of method 400.

A time window is identified, at 602. The time window identified at 602 may be desired to be significantly longer than the time interval for measurements (which is generally less than one minute). The time window is also desired to be less than not only the entire time period for which data is captured for a region (e.g. a month, a quarter, or a year), but also less than the time taken for a mobile sensor platform to traverse a route. For example, in some embodiments, the time window may be at least ten minutes and not more than two hours. In some embodiments, the time window may not exceed an hour (e.g. may be thirty minutes, forty-five minutes, or more). The size of the time window influences the magnitude of the anomaly likely to be detected. The longer the time window, the more local variability in measured concentrations is suppressed. Also at 602, the time step by which the time window is moved through a data set is determined. The step may be desired to be less than the length of the time window. For example, the step size may be ten seconds, twenty seconds, thirty seconds, one minute, or five minutes. In addition, the point of interest for the time window is determined at 602. For example, the point may be the center of the time window (e.g. 22.5 minutes into a forty-five-minute time window), at the start of the time window, or at the end of the time window.

Statistical values are determined for the sensor data of each time window, at 604. For example, suppose a particular route starts at 12:00 PM and ends at 8:00 PM; the time window is forty-five minutes, the step is ten seconds, and the point of interest is at the center of the time window. Thus, for time 12:22:30, the time window includes data for 12:00 PM through 12:45 PM. Statistical values are calculated for this window, at 604. The time window is advanced by ten seconds (i.e. the step). Statistical values are then calculated for time 12:22:40 and includes data for 12:10 PM through 12:45:10 PM. At 604, this process is carried out for the entire time of the route (e.g. 12:00 PM through 8:00 PM). Thus, the statistical values determined at 604 are for data that are close in time but may or may not be geographically close.

The temporal anomaly is identified based on the statistical values, at 606. In some embodiments, the temporal anomaly is associated with a position, such as a road segment. The temporal anomaly may be identified based on a normalized Z-score. This Z-score may be one of the statistical values determined at 604. For example, a temporal anomaly for a particular measured quantity may be identified if a particular road segment has a Z-score for the measured quantity in its time window in the upper ten percent of data analyzed for the route or for all routes. Other percentiles (e.g. the top fifteen percent or the top twenty percent) may be used. Anomaly detection may be further refined by requiring that the position have a threshold fraction of identifications as anomalous. For example, final identification as an anomaly may require that twenty percent of the passes for a road segment have the Z-score in the top ten percent.

Thus, using method 600, temporal anomalies may be detected. The anomalies detected may be based on the magnitude of the anomaly and the fraction of time the anomaly is observed when the position (e.g. road segment) is traversed. Using method 600, anomalies that may be obscured by aggregation can be observed. For example, a local source of a pollutant that is intermittent or otherwise short-lived might be identified using method 600. An intermittent signal may also reflect variability due to changes in transport and meteorology. Identifying these segments with high concentration features for some fraction of the single-pass data gives a separate way to assess and identify regions that may merit further investigation and/or application of mitigation strategies.

As part of anomaly identification at 606, the anomalies at positions (e.g. segments) may be classified. Anomalous positions are classified according to the different temporal characteristics and observed pollutant concentrations of the individual pass data for a given anomaly. In some embodiments, three criteria are used to classify anomalous segments; time of day, time of year, and high concentration measurements.

For example, segments having temporal anomalies may be classified as follows. Individual segments are classified into different temporal groups if at least forty percent (or another threshold) of all anomalies for that segment were observed during that temporal group. Temporal filtering may identify segments where the temporal group associated with the anomalous concentrations may provide information about the source type or atmospheric processing causing the anomaly. In some embodiments, additional criteria may be applied. In some embodiments, a segment may only be classified into a temporal group if the fraction of anomalies observed within the temporal group was at least as large as the fraction of all data collected within the time window. For example, if a segment had 75% of its data collected overnight and 60% of its anomalies were observed overnight, this segment may be falsely placed into the overnight time window group. Having a large portion of data collected overnight makes it difficult to distinguish if anomalies are truly more frequent overnight, or if they are evenly distributed throughout the day yet over-represented overnight due to the high fraction of overnight data collection. Having this extra criterion can prohibit falsely classifying segments into a temporal group due to imbalances in data collection.

Segments may also be also classified into sets that contained high concentration anomalies. This classification distinguishes the segments with anomalies that result from high concentrations, and are thus likely to be of concern, from those that have relatively low concentration anomalies.

Two other classification schemes can be used for classification based on concentration include (1) an absolute scheme, in which segments are classified if they contained an anomalous measurement with an associated concentration that was within the a certain percentage (e.g. the top 1%) of all concentrations observed; and (2) a relative scheme, where a segment may be classified as an anomaly if the segment contained an anomaly where the associated concentration measurement was at least a certain percentage (e.g. 100%, 200%, 300% or 400%) larger than other measurements associated with the segment. The absolute classification scheme includes anomalous segments where at least one of the anomalies was due to very high concentrations that may warrant further investigation. The relative scheme includes segments where at least one measurement is significantly higher than other measurements within the segment. Stated differently, the segment includes outliers that may be indicative of an exceptional event.

Figure 7:
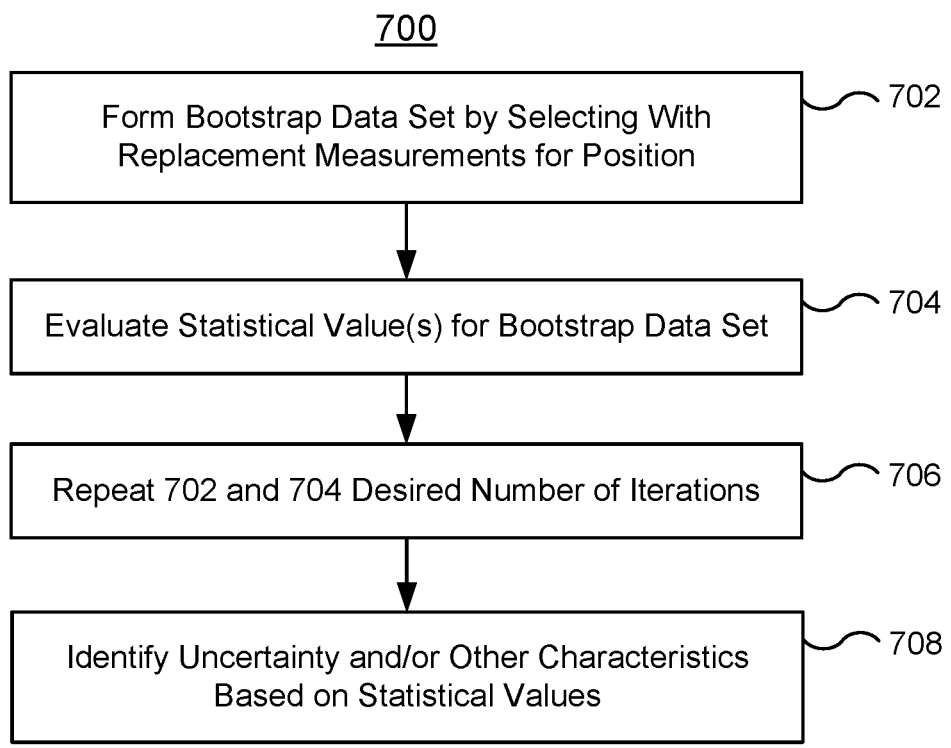
FIG. 7 is a flow chart depicting an embodiment of a method for determining an uncertainty level in environmental data.

FIG. 7 is a flow chart depicting an embodiment of method 700 for determining an uncertainty level in environmental data. Method 700 uses environmental data captured using mobile sensor platforms, such as mobile sensor platforms 102A, 102B and/or 102C. Method 700 is described in the context of system 100 but may be performed using other systems. For clarity, only some portions of method 700 are shown. Although shown in a sequence, in some embodiments, processes may occur in parallel and/or in a different order. The sensor data described herein may include environmental and/or air quality data including but not limited to particulate matter and gases described herein. Further, method 700 utilizes hyper-local data such as that captured using method 200 and processed as described in method 400. Method 700 may be performed for each position of interest to determine the uncertainty in statistical values calculated. For example, method 700 may be performed for each road segment. In some embodiments, method 700 may be performed for only a subset of the road segments fulfilling one or more criteria, such as having twenty passes. In some embodiments, method 700 is performed for statistical values that have been determined and for which the desired is desired to be determined. Although described in the context of measurements being in the data set, in some embodiments, means, medians, or other statistical values may be used as (i.e. replace) the measurement.

A bootstrap data set is provided for a position, at 702. This includes selecting with replacement a number of values from the measurements for the position. The selection of measurements at 702 may be random. For example, suppose a road segment has twenty measurements associated with it and the bootstrap data set is desired to include twenty values. At 702, twenty values are drawn from a pool of the measurements for the segment. A copy of the drawn measurement refills the place of the drawn measurement after each selection. Consequently, it is possible, though unlikely, that all of the twenty values drawn are the same measurement. Thus, the bootstrap data set may be formed.

The desired statistical value(s) are evaluated for the bootstrap data set, at 704. For example, the mean, median, and/or a particular percentile may be determined. At 706 the formation of the bootstrap data set and the evaluation of statistical values are repeated a desired number of times. Thus, a distribution of the statistical value(s) determined using the bootstrap data sets may be obtained at 706. As part of 706, 702, 704 and 706 may be repeated for each position of interest. Thus, the statistical values for multiple positions may be determined based on each position's bootstrap data sets.

Uncertainties in or other characteristics of the statistical value(s) are determined, at 708. For example, upper and lower thresholds may be determined at 708. The statistical values within these thresholds may be considered to have sufficiently high confidence. In some embodiments, for example, bounds of the $2.5^{th}$ percentile and the $97.5^{th}$ percentile are set. Segments having statistical values within these bounds (the "credible interval") are considered to have credible data. In some embodiments, an uncertainty score may be determined as part of 708. The uncertainty score may be the width of the credible interval divided by the statistical value that was calculated from the original data (rather than the bootstrap data set). This allows for a comparison of different segments.

Figure 8:
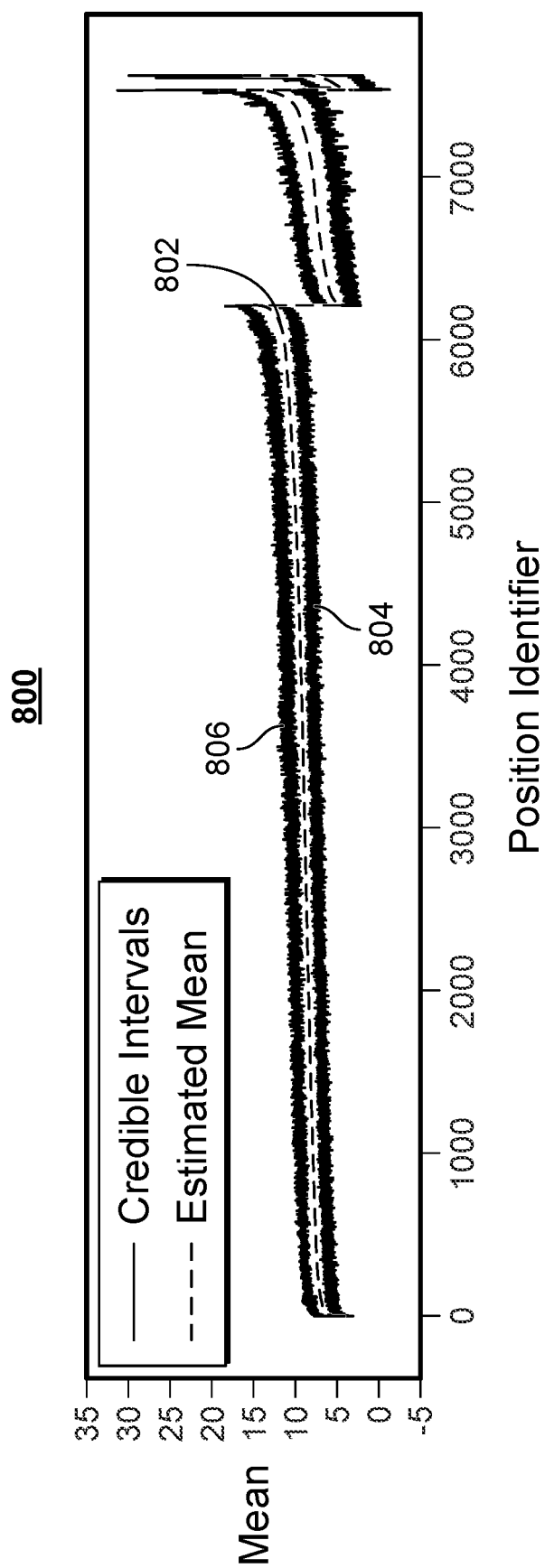
FIG. 8 is a graph depicting the uncertainty in a statistical value based on an embodiment of a method for determining uncertainty in environmental data.

FIG. 8 is a graph 800 depicting the uncertainty in the mean based on an embodiment of method 700. Although described in the context of the mean, analogous graphs may be generated for other statistical values, including but not limited to the median. Thus, for each segment of the over seven thousand segments shown, the bootstrap data set has been determined at 702, the mean determined at 704, and the process repeated to provide a distribution of the means. For graph 800, 708 includes providing upper and lower thresholds and defining a credible interval. Plot 802 indicates the mean determined for each segment using the actual measurements. Plots 804 and 806 indicate percentiles determined using the bootstrap data sets of method 700. For example, 804 may indicate the $2.5^{th}$ percentile, while 806 may indicate the $97.5^{th}$ percentile for each segment. The credible interval for the mean in graph 800 is between plots 804 and 806. Based on the credible interval, uncertainties in the mean may be estimated. Thus, using method 700, uncertainties in statistical values, such as the mean, may be determined and assessed.

Figure 9:
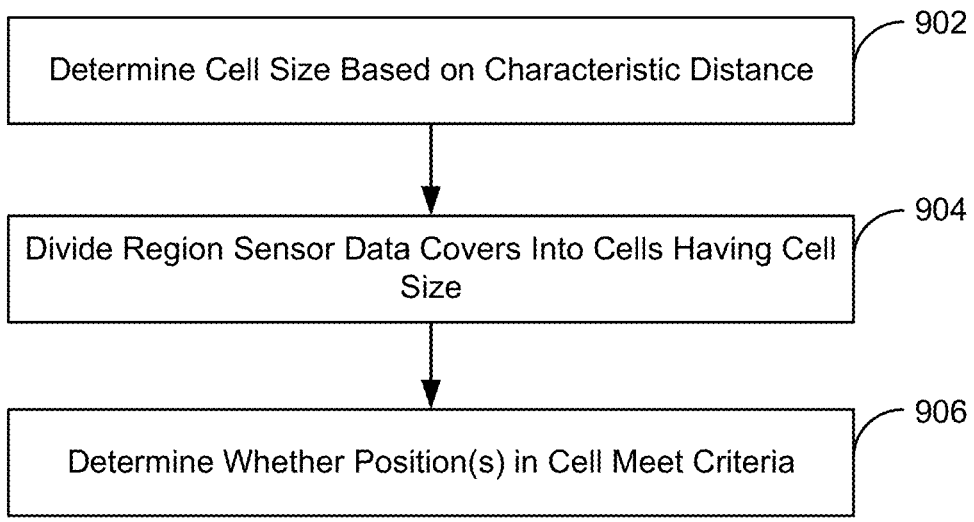
FIG. 9 is a flow chart depicting an embodiment of a method for determining characteristics of environmental data.

FIG. 9 is a flow chart depicting an embodiment of method 900 for determining characteristics of environmental data using the distribution formed using method 700. Thus, method 900 may be viewed as corresponding to 708 of method 700. Method 900 is described in the context of segments. However, other measures of position may be used.

The geographic region containing the segments may be desired to be divided into cells (e.g. hexagonal regions). To do so, the cell size is set based on the characteristic distance (e.g. the segment length), at 902. The cell size is set such that each cell includes multiple segments. The geographic region is divided into the cells, at 904. It is determined whether the segments in each cell meet particular criteria, at 906. Cells meeting these criteria may then be displayed or otherwise indicated (e.g. highlighted).

For example, suppose segments having an eighty percent probability that their mean concentration of PM2.5 is above ten micrograms per cubic meter are desired to be determined. Further, multi-segment trends are desired to be investigated for such segments. At 902 and 904 the cells size is defined and the geographic region divided into the cells. Suppose that cells having at least have of their segments meeting the above criteria are desired to be displayed. It is determined at 906 whether each cell in the geographic region meets these criteria. These cells may be highlighted. If the criteria are changed (e.g. cells having seventy-five percent of their segments with the defined probability are desired to be displayed or the concentration of PM2.5 is increased), the cells are redetermined at 906. The display may then be updated. Thus, changes in multi-segment regions may be indicated without aggregating data up to the cell level.

Figure 10:
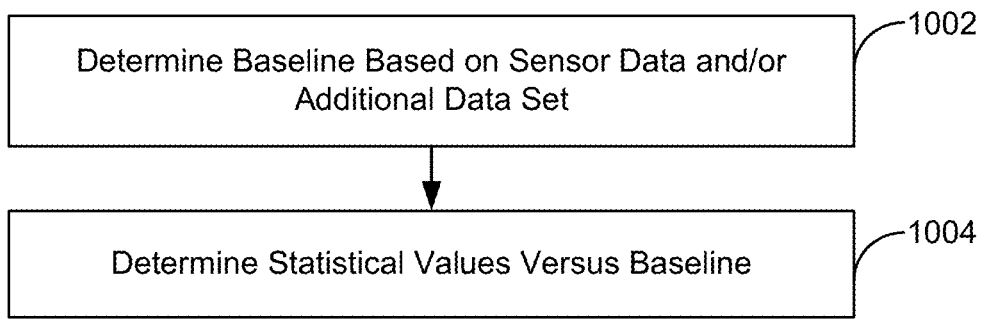
FIG. 10 is a flow chart depicting an embodiment of a method for determining a baseline for use in detecting anomalies and uncertainties in environmental data.

FIG. 10 is a flow chart depicting an embodiment of method 100 for determining a baseline for use in detecting anomalies and uncertainties in environmental data. Method 1000 uses environmental data captured using mobile sensor platforms, such as mobile sensor platforms 102A, 102B and/or 102C. Method 1000 is described in the context of system 100 but may be performed using other systems. For clarity, only some portions of method 1000 are shown. Although shown in a sequence, in some embodiments, processes may occur in parallel and/or in a different order. The sensor data described herein may include environmental and/or air quality data including but not limited to particulate matter and gases described herein. Further, method 1000 utilizes hyper-local data such as that captured using method 200 and processed as described in method 400. Method 1000 may be performed for each position of interest to determine the uncertainty in statistical values calculated. For example, method 1000 may be performed for each road segment.

The baseline is computed based on the measurements for each of the positions and/or additional data, at 1002. The additional data includes additional sensor data captured by another mobile sensor data platform and/or other data. Thus, the baseline may be determined based on the sensor data collected in a larger region over a longer time than a single sampling run and/or based on data from other sources. Other sources may include regulatory data, models, satellite data, meteorological data, and/or data from stationary sensor platforms.

Statistical values are determined based on the baseline, at 1004. For example, the difference between measurements (or statistical values) and the baseline may be determined. These values may be used to determine anomalies and/or other characteristics of the environmental data.

For example, the mean for PM2.5 data may be desired to be determined. However, PM2.5 may have a significant day-to-day and synoptic-scale variability. As a result, positions sampled on days when there are atypical levels of PM2.5 across the entire region (e.g., due to wildfires or inversions) may have means and/or other statistical values that are higher than other positions not sampled on those days. This sampling artifact creates the illusion of anomalies. Thus, the baseline determined using method 1000 may be desired for a better indication of the mean PM2.5 data.

The measured environmental data for PM2.5 can be normalized relative to the nearest representative, regulatory measurements to account for these variations in the background experienced by the entire region. In some embodiments, the regulatory and/or other data may be combined with other sensor data for the region captured using mobile sensor platforms. In particular, the PM2.5 baseline is determined to be the data measured by the nearest the regulatory station (reported hourly), at 1002. In some embodiments, an average of data from multiple nearby regulatory stations is used for the baseline at 1002. For example, the data may be weighted based on the proximity of the regulatory station. For each pass through a position (e.g. a segment), the difference between the PM2.5 levels observed in that segment and the baseline is calculated, at 1004. The difference reflects an enhancement or decrement relative to the regulatory station(s). The statistical values for the observed differences are determined and added to the mean PM2.5 level observed at the regulatory station(s) over the entire sensing period, at 1004. For example, the mean in the difference between the PM2.5 measurement and the baseline data may be determined at 1004. Also at 1004 this mean in the difference is added to the mean in the regulatory stations 2.5 data for the time period. This creates a background normalized estimate of the mean.

Using method 1000, variability in the background of environmental data may be determined and accounted for. As a result, statistical values calculated may better reflect the constituents of the environment (e.g. CO, PM2.5, $NO_2$, $CO_2$, etc.). Consequently, anomalies in the environmental data may be more accurately determined. Mitigation solutions and/or other responses to the abnormalities may, therefore, be better identified.

Although the foregoing embodiments have been described in some detail for purposes of clarity of understanding, the invention is not limited to the details provided. There are many alternative ways of implementing the invention. The disclosed embodiments are illustrative and not restrictive.

What is claimed is:

1. A method, comprising:
   receiving sensor data associated with each of a plurality of time intervals from at least one sensor on at least one mobile sensor platform, the sensor data being associated with position data corresponding to each of the plurality of time intervals, the position data corresponding to a plurality of positions having a characteristic distance not exceeding one hundred meters, the sensor data including a plurality of measurements for each of the plurality of positions;
   determining, based on the sensor data and the position data, anomalous data including a temporal anomaly, and wherein the determining of the anomalous data includes:
      defining a time window;
      determining, for each of a plurality of times, a plurality of statistical values for a portion of the sensor data in the time window corresponding to each of the plurality of times; and
      identifying the temporal anomaly based on the plurality of statistical values; and
   determining a mitigation strategy based on the temporal anomaly.

2. The method of claim 1, wherein the time window has a location with respect to each of the plurality of times, wherein the location is selected from one or more of the following: a center on each of the plurality of times and an endpoint on each of the plurality of times.

3. The method of claim 1, further comprising:
   determining a baseline for the sensor data, the baseline being computed based on the plurality of measurements for each of the plurality of positions and additional sensor data captured by a sensor data platform different from the at least one mobile sensor platform.

4. A method, comprising:
   receiving sensor data associated with each of a plurality of time intervals from at least one sensor on at least one mobile sensor platform, the sensor data being associated with position data corresponding to each of the plurality of time intervals, the position data corresponding to a plurality of positions having a characteristic distance not exceeding one hundred meters, the sensor data including a plurality of measurements for each of the plurality of positions;
   determining, based on the sensor data and the position data, anomalous data, wherein the anomalous data includes the geographic anomaly and wherein the determining of the anomalous data further includes:
      determining a plurality of statistical values for each of the plurality of positions for the sensor data;
      determining, for a radius greater than the characteristic distance and for each of the plurality of positions, a Gi* value for each of the plurality of statistical values; and
      identifying the geographic anomaly based on the Gi* value of each of the plurality of positions; and
   determining a mitigation strategy based on the geographic anomaly.

5. A method, comprising:
   receiving sensor data associated with each of a plurality of time intervals from at least one sensor on at least one mobile sensor platform, the sensor data being associated with position data corresponding to each of the plurality of time intervals, the position data corresponding to a plurality of positions having a characteristic distance not exceeding one hundred meters, the sensor data including a plurality of measurements for each of the plurality of positions;
   determining, based on the sensor data and the position data, anomalous data including at least one of a geographic anomaly or a temporal anomaly;
   determining an uncertainty for a statistical value for the sensor data, the determining the uncertainty further comprising, for each of the plurality of measurements for each of the plurality of positions
      selecting with replacement a number of measurements from the plurality of measurements to provide a bootstrap data set;
      evaluating a corresponding value for the statistical value for the number of measurements in the bootstrap data set;
      repeating the selecting and evaluating a particular number of times; and
      identifying the uncertainty based on the corresponding value for each bootstrap data set, comprising:
         setting an upper threshold and a lower threshold for the corresponding value; and
         dividing the statistical value by a difference between the upper threshold and the lower threshold; and
   determining a mitigation strategy based on the uncertainty.

6. The method of claim 5, wherein the identifying the uncertainty further includes:
  determining a cell size based on the characteristic distance;
  dividing a geographic region corresponding to the plurality of positions into a plurality of cells having the cell size, each cell including a portion of the plurality of positions; and
  for each cell, determining whether the portion of the plurality of positions meet at least one criterion.

7. A system, comprising:
  a processor configured to:
    receive sensor data associated with each of a plurality of time intervals from at least one sensor on at least one mobile sensor platform, the sensor data being associated with position data corresponding to each of the plurality of time intervals, the position data corresponding to a plurality of positions having a characteristic distance not exceeding one hundred meters, the sensor data including a plurality of measurements for each of the plurality of positions;
    determine, based on the sensor data and the position data, anomalous data including a temporal anomaly, comprises to:
      define a time window;
      determine, for each of a plurality of times, a plurality of statistical values for a portion of the sensor data in the time window corresponding to each of the plurality of times; and
      identify the temporal anomaly based on the plurality of statistical values; and
    determine a mitigation strategy based on the temporal anomaly; and
  a memory coupled to the processor and configured to provide the processor with instructions.

8. The system of claim 7, wherein the time window has a location with respect to each of the plurality of times, wherein the location is selected from one or more of the following: a center on each of the plurality of times and an endpoint on each of the plurality of times.

9. The system of claim 7, wherein the processor is further configured to:
  determine a baseline for the sensor data, the baseline being computed based on the plurality of measurements for each of the plurality of positions and additional sensor data captured by a sensor data platform different from the at least one mobile sensor platform.

10. A system, comprising:
  a processor configured to:
    receive sensor data associated with each of a plurality of time intervals from at least one sensor on at least one mobile sensor platform, the sensor data being associated with position data corresponding to each of the plurality of time intervals, the position data corresponding to a plurality of positions having a characteristic distance not exceeding one hundred meters, the sensor data including a plurality of measurements for each of the plurality of positions;
    determine, based on the sensor data and the position data, anomalous data, wherein the anomalous data includes the geographic anomaly and wherein to determine the anomalous data, the processor is further configured to:
      determine a plurality of statistical values for each of the plurality of positions for the sensor data;
      determine, for a radius greater than the characteristic distance and for each of the plurality of positions, a Gi* value for each of the plurality of statistical values; and
      identify the geographic anomaly based on the Gi* value of each of the plurality of positions; and
    determine a mitigation strategy based on the geographic anomaly; and
  a memory coupled to the processor and configured to provide the processor with instructions.

11. A system, comprising:
  a processor configured to:
    receive sensor data associated with each of a plurality of time intervals from at least one sensor on at least one mobile sensor platform, the sensor data being associated with position data corresponding to each of the plurality of time intervals, the position data corresponding to a plurality of positions having a characteristic distance not exceeding one hundred meters, the sensor data including a plurality of measurements for each of the plurality of positions;
    determine, based on the sensor data and the position data, anomalous data including at least one of a geographic anomaly or a temporal anomaly;
    determine an uncertainty for a statistical value for the sensor data, to determine the uncertainty, the processor being further configured to, for each of the plurality of measurements for each of the plurality of positions
      select with replacement a number of measurements from the plurality of measurements to provide a bootstrap data set;
      evaluate a corresponding value for the statistical value for the number of measurements in the bootstrap data set;
      repeat the selecting and evaluating a particular number of times; and
      identify the uncertainty based on the corresponding value for each bootstrap data set, comprises to:
        set an upper threshold and a lower threshold for the corresponding value; and
        divide the statistical value by a difference between the upper threshold and the lower threshold; and
    determine a mitigation strategy based on the uncertainty; and
  a memory coupled to the processor and configured to provide the processor with instructions.

12. The system of claim 11, wherein to identify the uncertainty, the processor is further configured to:
  determine a cell size based on the characteristic distance;
  divide a geographic region corresponding to the plurality of positions into a plurality of cells having the cell size, each cell including a portion of the plurality of positions; and
  for each cell, determine whether the portion of the plurality of positions meet at least one criterion.

13. A computer program product embodied in a non-transitory computer readable medium and comprising computer instructions for:
  receiving sensor data associated with each of a plurality of time intervals from at least one sensor on at least one mobile sensor platform, the sensor data being associated with position data corresponding to each of the plurality of time intervals, the position data corresponding to a plurality of positions having a characteristic distance not exceeding one hundred meters, the sensor data including a plurality of measurements for each of the plurality of positions;

determining, based on the sensor data and the position data, anomalous data including a temporal anomaly, and wherein the determining of the anomalous data includes:

defining a time window;

determining, for each of a plurality of times, a plurality of statistical values for a portion of the sensor data in the time window corresponding to each of the plurality of times; and identifying the temporal anomaly based on the plurality of statistical values; and determining a mitigation strategy based on the temporal anomaly.

14. The computer program product of claim 13, further comprising computer instructions for:

determining an uncertainty for a statistical value for the sensor data, the determining the uncertainty further comprising, for each of the plurality of measurements for each of the plurality of positions selecting with replacement a number of measurements from the plurality of measurements to provide a bootstrap data set;

evaluating a corresponding value for the statistical value for the number of measurements in the bootstrap data set;

repeating the selecting and evaluating a particular number of times; and identifying the uncertainty based on the corresponding value for each bootstrap data set.

15. The computer program product of claim 13, wherein the computer instructions further include computer instructions for:

determining a baseline for the sensor data, the baseline being computed based on the plurality of measurements for each of the plurality of positions and additional sensor data captured by a sensor data platform different from the at least one mobile sensor platform.

16. A computer program product embodied in a non-transitory computer readable medium and comprising computer instructions for:

receiving sensor data associated with each of a plurality of time intervals from at least one sensor on at least one mobile sensor platform, the sensor data being associated with position data corresponding to each of the plurality of time intervals, the position data corresponding to a plurality of positions having a characteristic distance not exceeding one hundred meters, the sensor data including a plurality of measurements for each of the plurality of positions;

determining, based on the sensor data and the position data, anomalous data, wherein the anomalous data includes the geographic anomaly and wherein the determining of the anomalous data further includes:

determining a plurality of statistical values for each of the plurality of positions for the sensor data;

determining, for a radius greater than the characteristic distance and for each of the plurality of positions, a $Gi^*$ value for each of the plurality of statistical values; and identifying the geographic anomaly based on the $Gi^*$ value of each of the plurality of positions; and determining a mitigation strategy based on the geographic anomaly.

17. A computer program product embodied in a non-transitory computer readable medium and comprising computer instructions for:

receiving sensor data associated with each of a plurality of time intervals from at least one sensor on at least one mobile sensor platform, the sensor data being associated with position data corresponding to each of the plurality of time intervals, the position data corresponding to a plurality of positions having a characteristic distance not exceeding one hundred meters, the sensor data including a plurality of measurements for each of the plurality of positions;

determining, based on the sensor data and the position data, anomalous data including at least one of a geographic anomaly or a temporal anomaly;

determining an uncertainty for a statistical value for the sensor data, the determining the uncertainty further comprising, for each of the plurality of measurements for each of the plurality of positions selecting with replacement a number of measurements from the plurality of measurements to provide a bootstrap data set;

evaluating a corresponding value for the statistical value for the number of measurements in the bootstrap data set;

repeating the selecting and evaluating a particular number of times; and identifying the uncertainty based on the corresponding value for each bootstrap data set, comprising:

setting an upper threshold and a lower threshold for the corresponding value; and dividing the statistical value by a difference between the upper threshold and the lower threshold; and determining a mitigation strategy based on the uncertainty.

* * * * *